United States Patent [19]

Shiokawa et al.

[11] Patent Number: 4,626,273
[45] Date of Patent: Dec. 2, 1986

[54] HERBICIDAL NOVEL 2-ALKOXYAMINOSULFONYL-BENZENE-SULFONYLUREAS

[75] Inventors: Kozo Shiokawa, Kawasaki; Toshio Goto, Sagamihara; Atsumi Kamochi, Hino; Koichi Moriya; Shigeo Kohama, both of Hachioji, all of Japan

[73] Assignee: Nihon Tokushu Noyaku Seizo K.K., Tokyo, Japan

[21] Appl. No.: 696,837

[22] Filed: Jan. 31, 1985

[30] Foreign Application Priority Data

Feb. 10, 1984 [JP] Japan .................................. 59-21839

[51] Int. Cl.$^4$ ..................... A01N 9/22; C07D 239/42
[52] U.S. Cl. .......................................... 71/92; 544/332
[58] Field of Search ........................... 544/332; 71/92

[56] References Cited

U.S. PATENT DOCUMENTS 4,310,346 1/1982 Levitt et al. ........................... 71/92

FOREIGN PATENT DOCUMENTS 0023141 1/1981 European Pat. Off. .

*Primary Examiner*—Richard L. Raymond
*Assistant Examiner*—James H. Turnipseed
*Attorney, Agent, or Firm*—Sprung Horn Kramer & Woods

[57] ABSTRACT

Novel herbicides are produced by the novel reaction

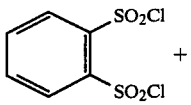

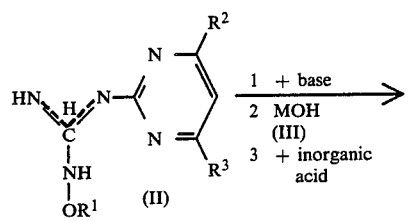

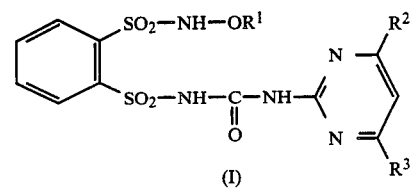

in which
R$^1$, R$^2$ and R$^3$ each independently is lower alkyl of 1 to 4 carbon atoms, and
M is an alkali metal atom.

8 Claims, No Drawings

HERBICIDAL NOVEL 2-ALKOXYAMINOSULFONYL-BENZENE-SULFONYLUREAS

DETAILED DESCRIPTION OF THE INVENTION

This invention relates to 2-alkoxyaminosulfonylbenzenesulfonyl urea derivatives, a process for production thereof, and their use as herbicides.

More specifically, this invention relates to 2-alkoxyaminosulfonylbenzene-sulfonylurea derivatives represented by the following general formula (I):

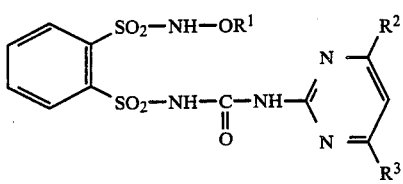

In the formula, each of $R^1$, $R^2$, and $R^3$ represents a lower alkyl group with 1-4 carbon atoms.

The compounds of general formula (I) can be produced by the following process to which the invention also pertains:

Process (i)

A process for producing the 2-alkoxyaminosulfonyl-benzene-sulfonylurea derivatives of general formula (1), which comprises reacting a compound of the formula

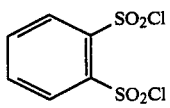

with a compound represented by the general formula

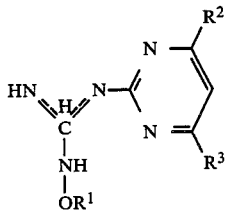

wherein $R^1$, $R^2$, and $R^3$ are as defined,
in the presence of a base, then reacting the product with an alkali metal hydroxide represented by the general formula

M—OH    (III)

wherein M represents an alkali metal atom, and further reacting the product with an inorganic acid.

The invention also relates to a herbicide comprising the 2-alkoxyaminosulfonylbenzene-sulfonylurea derivative of general formula (1) as an active ingredient.

Japanese Laid-Open Patent Publication No. 29563/1981 known before the filing of the present invention states that compounds of the general formula

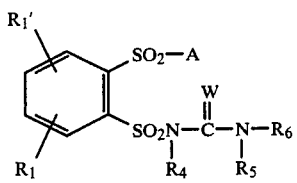

have herbicidal activity; and discloses a compound of the following formula:

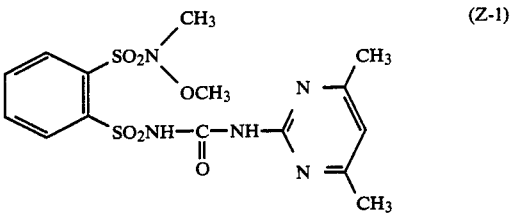

However, when A in general formula (Z) represents —$NR_2R_3$, the definitions of $R_2$ and $R_3$ in the above-cited Japanese patent document do not encompass a compound corresponding to A=—NH—$OR^1$ specified in the present invention. The compounds of formula (1) of this invention cannot be produced by the process disclosed in the above patent document, and can be produced by the process of this invention described above.

The present inventors have made extensive investigations in order to create novel compounds having herbicidal activity. Consequently, they have succeeded in synthesizing the compounds of general formula (I) and found that these compounds have excellent herbicidal activity. These findings have led to the accomplishment of the present invention.

To the best of the knowledges of the present inventors, the compounds of general formula (I) in accordance with this invention are novel compounds not described in known publications published before the filing of the present application. The compounds of this invention are characterized by the fact that as shown by general formula (I), their chemical structure has an N-benzenesulfonyl N'-(4,6-dialkylpyrimidin-2-yl)urea as a basic skeleton and an alkoxyaminosulfonyl group is substituted at the 2-position of the benzene. The compound of this invention is similar in chemical structure to the compounds disclosed in the above-cited Japanese Laid-Open Patent Publication No. 29563/1981. It has been found however that the compounds of this invention having the aforesaid characteristic chemical structure can be produced only by the process (i) in accordance with this invention, and cannot be obtained by the process for producing the compounds specified in the above-cited Japanese Laid-Open Patent Publication No. 29563/1981.

Biologically, the compounds of this invention have excellent selective herbicidal activity for upland farming in that they have strong herbicidal activity against upland farm weeds and do not cause phytotoxicity to upland farm crops such as soybean and winter wheat. It has been found that the above activity is exhibited only in relation to the chemical structure shown by the above general formula.

The compounds of this invention can be easily produced, for example, by the process (i) shown above.

It is an object of this invention therefore to provide the novel 2-alkoxyaminosulfonylbenzene-sulfonylurea derivatives of general formula (I), a process for production thereof and the use thereof as a herbicide.

The above and other objects of this invention will become more apparent from the following description.

The compounds of this invention can be conveniently used as a herbicide for weed control because they have low toxicity and good selectivity for cultivated plants, or in other words, they have no phytotoxicity to cultivated plants at usual dosages. The herbicide of this invention exhibits an outstanding selective controlling efficacy particularly when used against a broad range of upland farm weeds as a pre-emergence soil treating agent or a foliar and soil treating agent.

The compounds of general formula (I) in accordance with this invention have high safety and exhibit an outstanding herbicidal efficacy.

The herbicidal spectrum of these compounds shows that they have a strong herbicidal efficacy against, for example, Alopecurus aequalis Sobol. var. amurensis Ohwi,
Setaria glauca P. Beavu.,
Stellaria media Villars,
Echinochloa crus-galli P. Beauv.,
Digitaria adscendens Henr.,
Eleusine indica Gasrin.,
Digitaria violascens Link,
Amaranthus lividus Loisel.,
Polygonum blumei Meisn.,
Chenopodium album L.,
Chenopodium ficifolium Smith,
Amaranthus refroflexus L.,
Poa annua L.,
Rorippa palustris Bess.,
Polygonum nepalense Meisn.,
Rumex obtusifolius L.,
Rumex japonicus Houtt.,
Lamium amplexicaule L.,
Galium spurium L.,
Stellaria alsine Grimm,
Cardamine flexuosa With., and
Polygonum ariculare L.

The herbicide of this invention can be used safely without a damaging action on many crops such as beans, wheat, cotton, carrot, potato, beat, cabbage, mustards, peanuts, radish, tobacco, tomato and cumumber.

The applicability of the active compounds of this invention is not limited to upland farm weeds, and they are also effective against weeds detrimental to rice and rush, and weeds occurring in lands temporarily out of cultivation. The term "weeds", as used herein, means all plants which grow in undesired places in the broadest sense.

The compounds of general formula (I) in accordance with this invention can be produced, for example, by the following process (i):

Process (i)

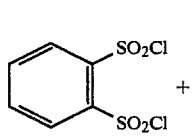

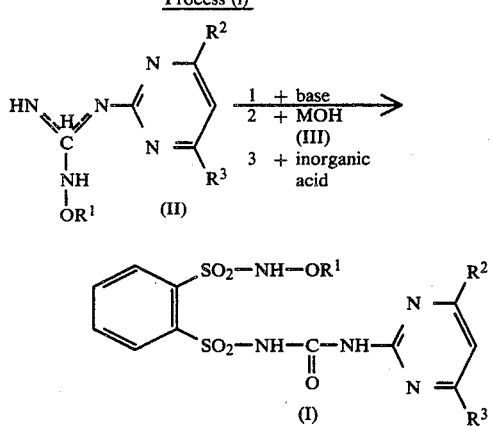

In the formulae, $R^1$, $R^2$, $R^3$, and M are as defined hereinabove.

In the above reaction scheme, each of $R^1$, $R^2$, and $R^3$ represents a lower alkyl with 1–4 carbon atoms, such as methyl, ethyl, propyl, isopropyl, and n-(iso-, sec-, or tert-)butyl.

M represents an alkali metal atom, such as lithium, sodium and potassium.

Specific examples of the compounds of general formula (II) as a starting material in the above general formula are N-(4,6-dimethylpyrimidin-2-yl) N'-methoxyguanidine, and N-(4,6-dimethylpyrimidin-2-yl) N'-ethoxyguanidine.

Specific examples of the alkali metal hydroxide of general formula (III) include sodium hydroxide, potassium hydroxide and lithium hydroxide.

Specific examples of the inorganic acid are hydrochloric acid and sulfuric acid.

Pyridine can be cited as a specific example of the base.

By citing the following typical example, the above process will be specifically described.

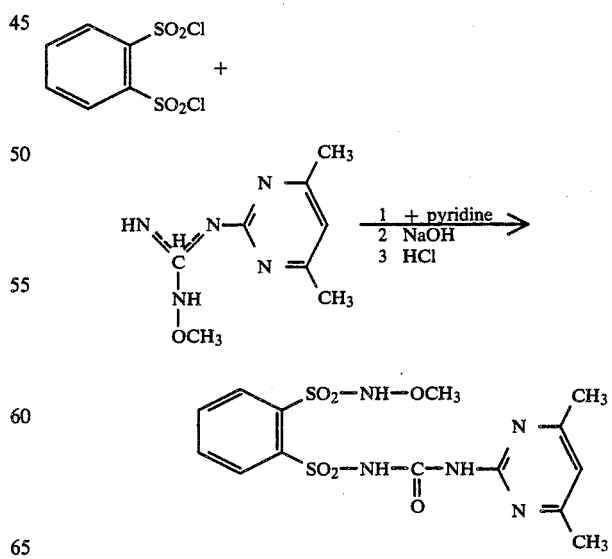

Desirably, the above process for producing the compound of this invention can be carried out using a solvent or a diluent. For this purpose, all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above reaction may be carried out in the presence of an acid binder. Examples of the acid binder include the hydroxides, carbonates, bicarbonates and alcoholates of alkali metals and tertiary amines such as triethylamine, diethylaniline and pyridine, all of which are generally used.

The above process can be carried out over a wide temperature range. Generally, it can be carried out at a temperature between about $-20°$ C. and the boiling point of the mixture, desirably between about $0°$ C. and about $100°$ C. Desirably, the reaction is carried out under normal atmospheric pressure, but it is also possible to operate under elevated or reduced pressures.

As a herbicide, the compounds of formula (I) in accordance with this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herein include, for example, diluents (solvents, extenders, carriers), surface-active agents (solubilizing agents, emulsifiers, dispersing agents, wetting agents), stabilizers, stickers, aerosol propellants and synergists.

Examples of the solvents are water, and organic solvents, for example hydrocarbons [such as n-hexane, petroleum ether, petroleum fractions (e.g., paraffin waxes kerosene, light oils, middle oils and heavy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol), ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as dimethylformamide and dimethylacetamide) and sulfoxides (such as dimethyl sulfoxides).

Examples of the extenders or carriers include inorganic powders, for example sulfur, slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofluoromethane, dichlorofluoromethane, 1,2,2-trichloro-1,1,2-trifluoroethane, chlorobenzene, LNG, and lower ethers); combustion controlling agents for fumigants (such as nitrites, zinc powder, and dicyandiamide); oxygen-yielding agents (such as chlorates); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, oil preparations, wettable powders, soluble powders, suspensions, dusts, granules, and pulverulent preparations.

The herbicide of this invention may contain about 0.001 to about 100% by weight, preferably about 0.005 to about 95% by weight, of the aforesaid active ingredient.

In actual use, the suitable amount of the active compound in the aforesaid various formulations and ready-to-use preparations is generally about 0.01 to about 95% by weight, preferably about 0.05 to about 60% by weight.

The content of the active ingredient can be properly varied depending upon the type of the formulation, the method, purpose, time and locus of its application, and the state of occurrence of weeds.

If required, the compounds of this invention may be used in combination with other agricultural chemicals, for example insecticides, fungicides, miticides, nematocides, antiviral agents, other herbicides, plant growth regulators and attractants [such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds], and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); and soil application (mixing, sprinkling, etc.). It can also be used by the so-called ultralow volume spraying method. According to this method, the active ingredient may be included in an amount of 100%.

The rate of application per unit area is, for example, about 0.005 to about 3 kg, preferably about 0.01 to about 1 kg, per hectare. In special cases, however, it may, and sometimes should, be outside the specified range.

According to this invention, there can be provided a herbicidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling weeds, which comprises applying to weeds and/or their habitat the compound of general formula (I) either singly or in admixture with a diluent (a solvent and/or an extender and/or a carrier) and/or a surface-active agent and if further required, a stabilizer, a sticker, a synergist, etc.

The following examples illustrate the present invention specifically. It should be noted however that the invention is not limited to these specific examples alone.

EXAMPLE 1

N-(4,6-dimethylpyrimidin-2-yl) N'-methoxyguanidine (1.95 g) was dissolved in pyridine (50 ml), and 1,2-benzenesulfonyl chloride (2.75 g) was added. The mixture was stirred for one day at room temperature. After the reaction, pyridine was evaporated under reduced pressure from the reaction mixture. A 2N aqueous solution of sodium hydroxide (50 ml) was added to the residue, and the mixture was stirred at room temperature for 1 hour. When the aqueous alkali solution was adjusted to pH 1 with hydrochloric acid, crude crystals precipitated. The crystals were collected by filtration, and recrystallized from acetonitrile to give the desired N-(2-methoxyaminosulfonylbenzenesulfonyl) N'-(4,6-dimethylpyrimidin-2-yl)urea (2.5 g) represented by the following formula, mp. 218°–219° C.:

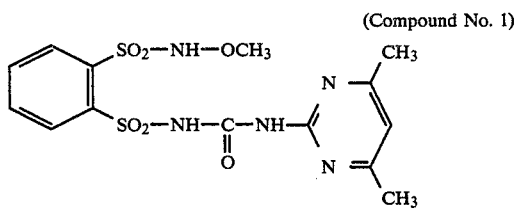
(Compound No. 1)

The structure of the above compound was analyzed and determined by X-ray diffraction.

By nearly the same method as in Example 1, N-(2-ethoxyaminosulfonylbenzenesulfonyl) N'-(4,6-dimethylpyrimidin-2-yl)urea represented by the following formula was synthesized:

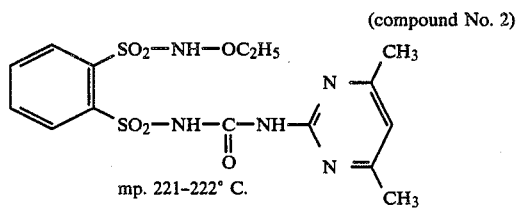
(compound No. 2)
mp. 221–222° C.

The compounds shown in Table 1 below were synthesized by much the same method as in Example 1 using suitably selected guanidines of general formula (II), alkali metal hydroxides of general formula (III) and inorganic acids.

TABLE 1

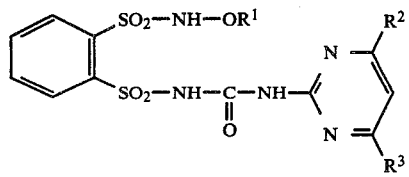

| Compound No. | $R^1$ | $R^2$ | $R^3$ | Physical constants |
|---|---|---|---|---|
| 3 | —CH$_3$ | —C$_2$H$_5$ | —C$_2$H$_5$ | |
| 4 | —CH$_3$ | —C$_3$H$_7$—n | —C$_3$H$_7$—n | |
| 5 | —CH$_3$ | —C$_3$H$_7$—iso | —C$_3$H$_7$—iso | |
| 6 | —C$_2$H$_5$ | —C$_2$H$_5$ | —C$_2$H$_5$ | |
| 7 | —C$_3$H$_7$—n | —CH$_3$ | —CH$_3$ | mp. 212° C. (decomp.) |
| 8 | —C$_4$H$_9$—n | —CH$_3$ | —CH$_3$ | mp. 169° C. |
| 9 | —C$_3$H$_7$—iso | —CH$_3$ | —CH$_3$ | mp. 218° C. (decomp.) |
| 10 | —CH$_3$ | —C$_4$H$_9$—n | —C$_4$H$_9$—n | |

EXAMPLE 2

(wettable powder)

Fifteen parts of compound No. 1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and dropped onto weeds and/or their habitat.

EXAMPLE 3

(emulsifiable concentrate)

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and dropped onto weeds and/or their habitat.

EXAMPLE 4

(dust)

Two parts of compound No. 1 of the invention and 98 parts of powdery clay are pulverized and mixed to form a dust. It is scattered over weeds and/or their habitat.

EXAMPLE 5

(dust)

Compound No. 2 of the invention (1.5 parts), 0.5 part of isopropyl hydrogen phosphate (PAP) and 98 parts of powdery clay are pulverized and mixed to form a dust. It is scattered over weeds and/or their habitat.

EXAMPLE 6

(granules)

Water (25 parts) is added to a mixture consisting of 10 parts of compound No. 1 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over weeds and/or their habitat.

EXAMPLE 7

(granules)

Ninety-five parts of clay mineral particles having a particle size distribution between 0.2 and 2 mm are put in a rotary mixer, and with rotation, 5 parts of compound No. 15 of the invention dissolved in an organic solvent is sprayed onto the particles to wet them uniformly to form granules. They are then dried at 40° to 50° C. The granules are scattered over weeds and/or their habitat.

EXAMPLE 8

(biological test)

Test for post-emergence foliar treatment of upland farm weeds and crops:

Preparation of an active compound

Carrier: 5 parts by weight of acetone
Emulsifier: 1 part by weight of benzyloxy polyglycol ether A preparation of the active compound was formed by mixing one part by weight of the active compound and the amount amounts of the carrier and emulsifier to give an emulsifiable concentrate, and diluting it with water to a predetermined concentration.

Testing method

In a greenhouse, seeds of wheat were sown in pots (1000 cm$^2$) filled with upland farm soil, and soil containing the seeds of *Alopecurus aequalis* Sobol. var. amurensis Ohwi., *Stellaria media* Villars, and *Stellaria alsine* Grimm was laid over them to a depth of 1 cm.

Ten days after germination (when the wheat and weeds were in the two-leaf stage), each of the chemicals prepared as above to a predetermined concentration was uniformly sprayed onto the surface layer of the soil in each of the pots.

Four weeks after spraying, the herbicidal efffect and the degree of phytotoxicity to wheat were examined on the following standards.

Evaluation of the herbicidal effect (herbicidal rate based on the non-treated area):
5: at least 95% (withered)
4: at least 80% but less than 95%
3: at least 50% but less than 80%
2: at least 30% but less than 50%
1: at least 10% but less than 30%
0: less than 10% (no effect)

Evaluation of phytotoxicity to wheat (the phytotoxicity rate based on the non-treated area):
5: at least 90% (fatal injury)
4: at least 50% but less than 90%
3: at least 30% but less than 50%
2: at least 10% but less than 30%
1: more than 0% but less than 10%
0: 0% (no phytotoxicity)

A phytotoxicity index of 2 or more represents lack of practical use.

The test results are shown in Table 2.

TABLE 2

| Compound No. | Amount of the active ingredient (kg/ha) | Herbicidal effect | | | Phytotoxicity to wheat |
|---|---|---|---|---|---|
| | | A. aequalis | S. media | S. alsine | |
| 1 | 0.05 | 5 | 5 | 5 | 0 |
| | 0.01 | 4 | 5 | 5 | 0 |
| 2 | 0.05 | 5 | 5 | 5 | 0 |
| | 0.01 | 4 | 5 | 5 | 0 |
| Control | 0.05 | 5 | 5 | 5 | 2 |
| Z-1 | 0.01 | 2 | 4 | 3 | 0 |
| Simazine | 0.4 | 3 | 5 | 5 | 1 |

Note
1. Simazine (commercial product): 2-chloro-4,6-bis(ethylamino)-1,3,5-triazine, 50% wettable powder.
2. Z-1:

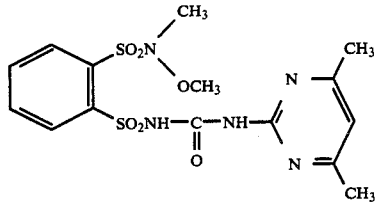

(the compound described in Japanese Laid-Open Patent Publication No. 29563/1981)

EXAMPLE 9

(biological test)

Test for pre-emergence soil treatment on upland farm weeds and crops:

Testing method

In a greenhouse, soybean seeds were sown on 1000 cm$^2$ pots filled with upland farm soil, and soil containing seeds of *Digitaria adscendens* Henr., *Amaranthus lividus* Loisel., *Chenopodium album* L., and *Echinochloa crusgalli* P. Beauv. was put over them to a depth of 1 cm. One day after the sowing and soil covering, the chemical prepared was uniformly sprayed in a predetermined concentration onto the surface layer of the soil in each of the pots.

Four weeks after the spraying, the herbicidal effect and the degree of phytotoxicity to soybean were examined in accordance with the same standards as in Example 8.

The results are shown in Table 3.

TABLE 3

| Compound | Amount of the active ingredient (kg/ha) | Herbicidal effect | | | | Phytotoxicity to soybean |
|---|---|---|---|---|---|---|
| | | D. adscendens | A. lividus | C. album | E. crusgalli | |
| 1 | 0.1 | 5 | 5 | 5 | 5 | 0 |
| 2 | 0.1 | 5 | 5 | 5 | 5 | 0 |
| Control | | | | | | |
| Z-1 | 0.1 | 5 | 5 | 5 | 5 | 3 |
| Simazine | 0.4 | 3 | 3 | 5 | 5 | 1 |

Note:
Z-1 and Simazine are the same as in Table 2.

It will be understood that the specification and examples are illustrative but not limitative of the present invention and that other embodiments within the spirit and scope of the invention will suggest themselves to those skilled in the art.

What is claimed is:

1. A 2-alkoxyaminosulfonylbenzene-sulfonylurea of the formula

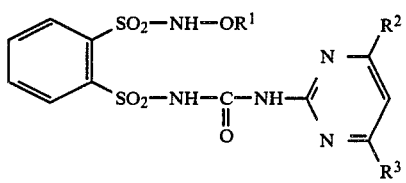

in which $R^1$, $R^2$ and $R^3$ each independently is a lower alkyl group with 1-4 carbon atoms.

2. A compound according to claim 1, wherein such compound is N-(2-methoxyaminosulfonylbenzenesulfonyl) N'-(4,6-dimethylpyrimidin-2-yl)urea of the formula

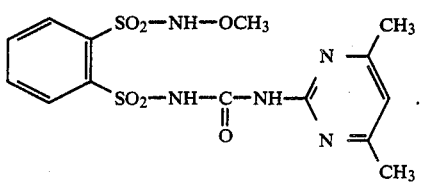

3. A compound according to claim 1, wherein such compund is N-(2-ethoxyaminosulfonylbenzenesulfonyl) N'-(4,6-dimethylpyrimidin-2-yl)urea of the formula

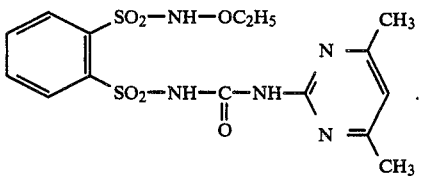

4. A process for producing a 2-alkoxyaminosulfonyl-benzene-sulfonylurea according to claim 1 which comprises reacting a compound of the formula

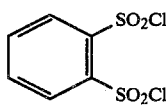

with a compound of the formula

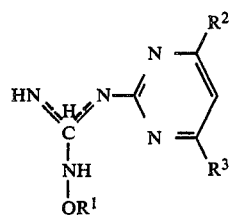

in the presence of a base, then reacting the product with an alkali metal hydroxide and further reacting the product with an inorganic acid.

5. A herbicidal composition comprising a herbicidally effective amount of a compound according to claim 1 in admixture with a diluent.

6. A method of combating unwanted vegetation which comprises applying to such vegetation or to a locus from which it is desired to exclude such vegetation a herbicidally effective amount of a compund according to claim 1.

7. The method according to claim 6, wherein such compound is N-(2-methoxyaminosulfonylbenzenesulfonyl) N'-(4,6-dimethylpyrimidin-2-yl)urea.

8. The method according to claim 6, wherein such compound is N-(2-ethoxyaminosulfonylbenzenesulfonyl) N'-(4,6-dimethylpyrimidin-2-yl)urea.

* * * * *